(12) United States Patent
Ierulli et al.

(10) Patent No.: US 10,010,442 B2
(45) Date of Patent: Jul. 3, 2018

(54) NASAL DILATOR WITH ELASTIC MEMBRANE STRUCTURE

(71) Applicants: Joseph V. Ierulli, Portland, OR (US); Edmund A. Sinda, Sarasota, FL (US)

(72) Inventors: Joseph V. Ierulli, Portland, OR (US); Edmund A. Sinda, Sarasota, FL (US)

(73) Assignees: Corbett Lair Inc., Bradenton, FL (US); Aso LLC, Sarasota, FL (US)

( * ) Notice: Subject to any disclaimer, the term of this patent is extended or adjusted under 35 U.S.C. 154(b) by 206 days.

(21) Appl. No.: 14/677,897

(22) Filed: Apr. 2, 2015

(65) Prior Publication Data

US 2016/0008161 A1    Jan. 14, 2016

Related U.S. Application Data

(60) Provisional application No. 61/980,813, filed on Apr. 17, 2014.

(51) Int. Cl.
| | |
|---|---|
| *A61F 5/08* | (2006.01) |
| *A61F 13/12* | (2006.01) |
| *A61M 16/00* | (2006.01) |
| *A61F 5/01* | (2006.01) |
| *A62B 7/00* | (2006.01) |

(52) U.S. Cl.
CPC .............. *A61F 5/08* (2013.01); *A61F 13/126* (2013.01); *A61F 2005/0197* (2013.01); *A61F 2210/0076* (2013.01); *A61M 16/00* (2013.01); *A61M 2210/0618* (2013.01); *A62B 7/00* (2013.01)

(58) Field of Classification Search
CPC .. A61F 13/126; A61F 5/08; A61F 2005/0197; A61F 2210/0076; A62B 7/00; A61M 16/00; A61M 2210/0618
See application file for complete search history.

(56) References Cited

U.S. PATENT DOCUMENTS

| | | | | |
|---|---|---|---|---|
| 5,533,503 | A | * | 7/1996 | Doubek ..................... A61F 5/08 128/200.24 |
| 5,957,126 | A | * | 9/1999 | Neeser ....................... A61F 5/08 128/200.24 |
| 2011/0166594 | A1 | * | 7/2011 | Eull ........................... A61F 5/08 606/201 |

* cited by examiner

*Primary Examiner* — Robert Lynch
(74) *Attorney, Agent, or Firm* — Mersenne Law

(57) ABSTRACT

An external nasal dilator comprises resilient and engagement elements. The engagement element functions primarily to affix, adhere, or otherwise engage the dilator to the skin surface of the nose. The resilient element comprises one part that provides out-of-plane resiliency, or spring biasing forces, and another part that provides in-plane elasticity, or stretching or tensioning forces. The dilator includes horizontal regions adapted to engage outer wall tissues of first and second nasal passages of a nose. When in use the dilator stabilizes or expands nasal outer wall tissues and prevents the outer wall tissues from drawing inward during breathing.

17 Claims, 12 Drawing Sheets

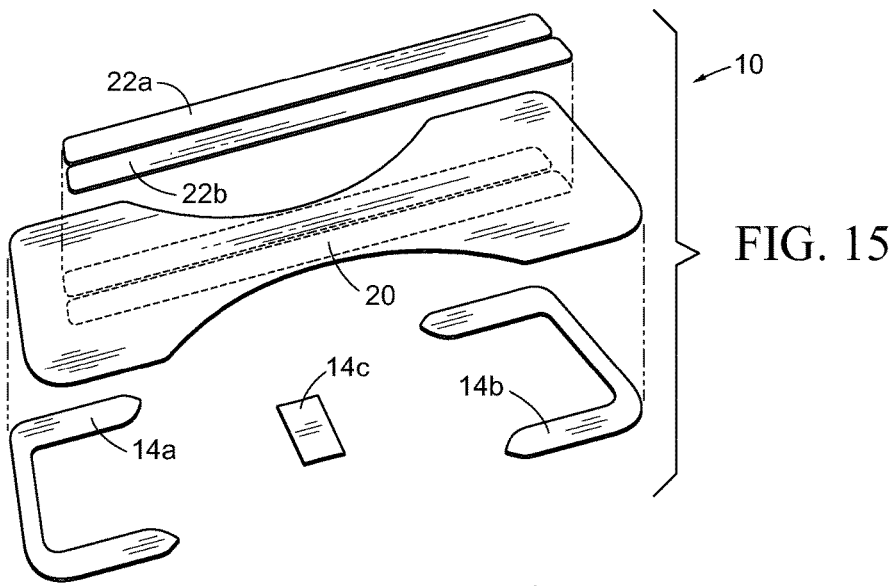
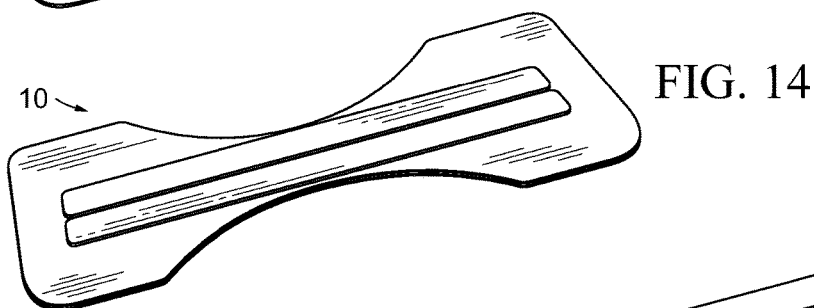
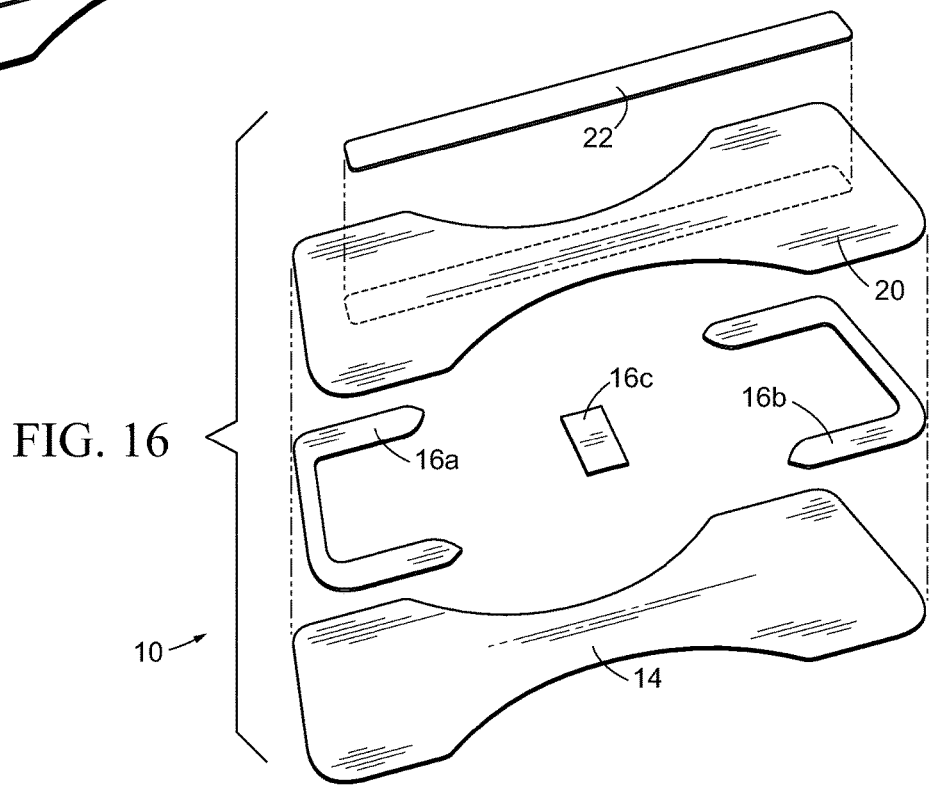

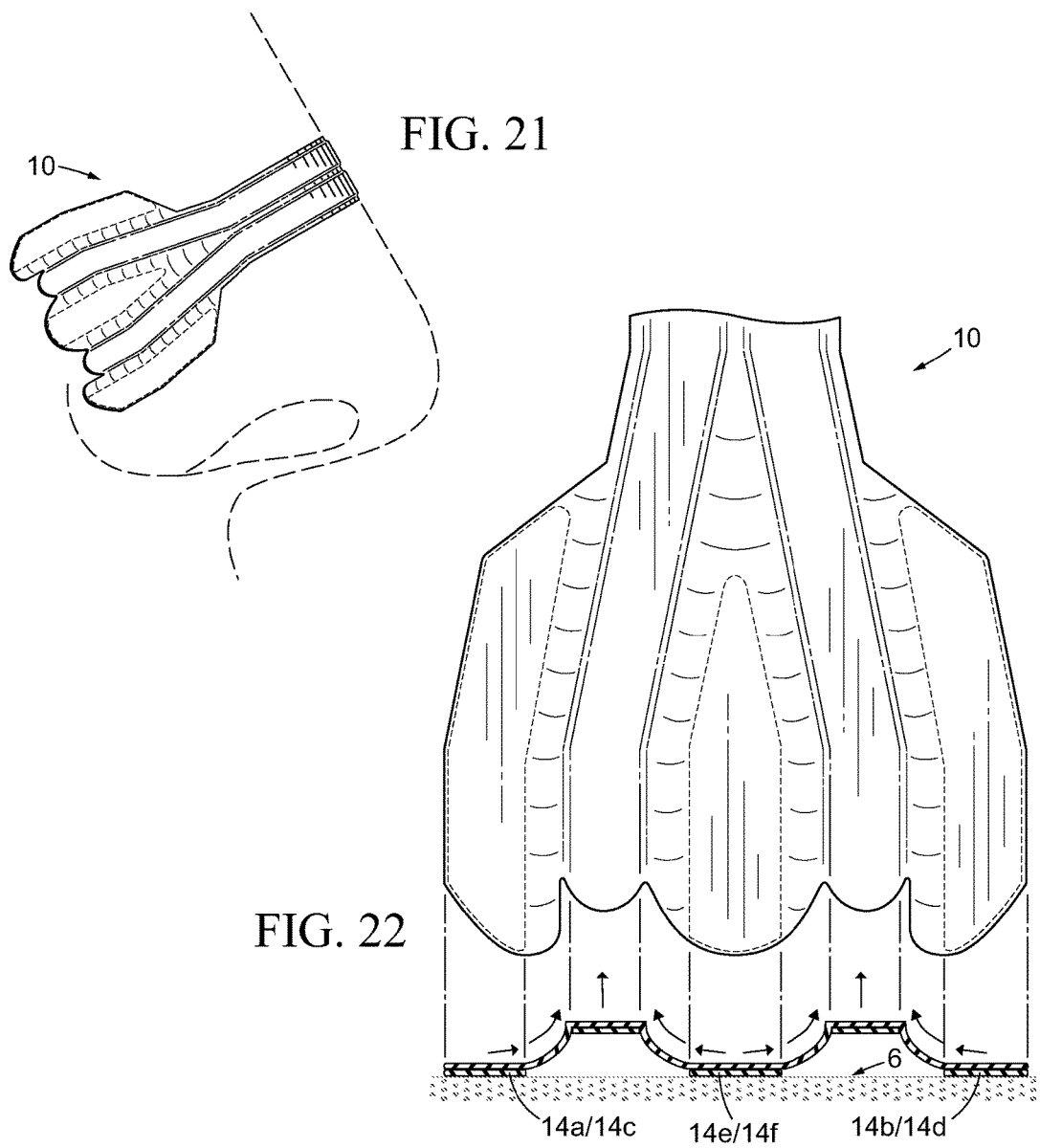
FIG. 21
FIG. 22
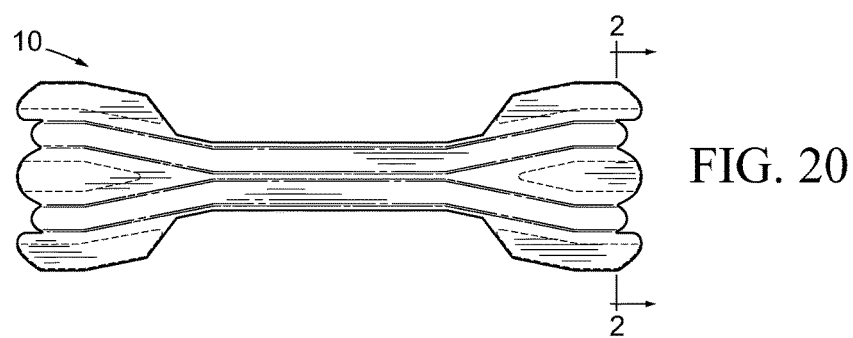
FIG. 20

NASAL DILATOR WITH ELASTIC MEMBRANE STRUCTURE

RELATED APPLICATIONS

The present application claims priority benefit to U.S. Provisional Patent Application No. 61/980,813 filed 17 Apr. 2014.

FIELD OF THE INVENTION

The present invention relates generally to medical devices, and more particularly to apparatus for and methods of supporting and stabilizing or dilating external tissue in humans. As disclosed and taught in the preferred embodiments, the tissue dilator devices are particularly suitable for, and are directed primarily to, external nasal dilators for supporting, stabilizing, and dilating nasal outer wall tissues adjacent and overlying nasal airway passages of the human nose, including the nasal valve and the nasal vestibule areas thereof. The United States Food and Drug Administration classifies the external nasal dilator as a Class I Medical Device. The present invention may also be sized, configured, or adapted to externally support or stabilize tissue, or inhibit torsion or movement, in other parts of the human body such as the lower or upper back, shoulder, neck, arm, calf, thigh, etc.

BACKGROUND OF THE INVENTION

External nasal dilators worn on the skin surface of the human nose are well disclosed in the art. In use the external nasal dilator is flexed across the bridge of the nose, engaging the nasal passage outer wall tissues on each side of the bridge, and held thereto by adhesive.

A resilient member (synonymously referred to in the art as a spring, spring member, resilient band, resilient member band, spring band, or bridge) extends along the length of the device, secured to a thin, flexible sheet or sandwiched between two thin flexible sheets. Flexed across the bridge of the nose, the resilient member exerts spring biasing forces that urge the nasal outer wall tissues outward, stabilizing, expanding dilating the nasal passageways. Stabilized or dilated tissue reduces nasal airflow resistance within the nasal passages, promoting a corresponding increase, ease, or improvement in nasal breathing. Increased nasal airflow may have beneficial effects generally; for example, more restful or restorative sleep, or beneficial effects with regard to nasal congestion, nasal snoring or obstructive sleep apnea. External nasal dilators have been shown to have beneficial effects for athletes, particularly in sports where a mouthguard is worn.

A particular inherent limitation of the external nasal dilator is peel forces generated by the dilator's resilient member(s) that, together with some tensile forces, act to disengage, or delaminate, the device from the skin surface. It is desirable to include design attributes in dilator devices that mitigate delaminating effects, or that otherwise shift at least a portion of peel forces into shear forces. The present invention builds upon the prior art in this regard, using an elastic membrane, or web, as part of the resilient element.

SUMMARY OF THE INVENTION

Nasal dilator devices of the present invention comprise resilient and engagement elements. The engagement element functions primarily to affix, adhere, or engage the dilator to the skin surface of the nose overlying the nasal passages. The resilient element comprises a first part in the form of at least one resilient member that provides resiliency, or spring biasing forces, extending generally perpendicular to, or obliquely from, a surface plane thereof. The resilient element further comprises a second part in the form of an elastic membrane that provides elasticity, or stretching, tensing, or tensioning forces, extending generally parallel to a surface plane thereof. The dilator may also include a directional element that affects its spring biasing properties.

The elastic, or tensioning, force, directs dilator spring biasing, at least in part, as more fully described below. The dilator engagement element, by itself, provides little or no nasal dilation (although depending on the material used, could provide some stabilization to the outer walls of the nasal passages). The resilient element, by itself and affixed to the skin by adhesive, generally will not remain well engaged thereto. Accordingly, nasal dilators of the present invention preferably combine separate resilient and engagement elements in a single body truss.

Nasal dilators of the present invention are capable of resilient and elastic deformation by virtue of the resilient element. That is, when released after flexure the dilator returns to a substantially planar or pre-flexed state. In use the dilator stabilizes the nasal outer wall tissues and prevents the tissue from drawing inward during breathing. The dilator is further designed to expand, or dilate, the nasal passages. The dilator engages comfortably to the nose and is easily removed with little or no stress to the skin.

Dilators of the present invention generate a most preferred range of from about 15 grams to about 35 grams of resiliency, or spring biasing force, for non-athletes, and may generate from about 25 grams to about 45 grams for athletes. Less than 10 grams may not provide enough stabilization or dilation for some users, while greater than 35 grams may be uncomfortable for most home users. Overall spring biasing force is determined by the configuration of the resilient element: the width, length, and thickness of one or more resilient members, the type of resilient member material used, and the configuration of the elastic membrane and its material properties. Dilators are usually manufactured in the unflexed, unstretched, initial position, and are flexed and/or stretched during application. Thus, embodiments may be described either as "capable of" flexing and/or stretching (when the embodiment is in an initial or rest position) or "flexed" and/or "stretched" (when the embodiment is in use).

The dilator's resilient member(s) are semi-rigid; they flex out-of-plane and possess little or no in-plane stretch. The elastic membrane stretches in-plane, and may be flexible out of plane. The terms spring biasing, spring biasing force, spring force, resiliency, spring constant, etc. as used herein are generally synonymous, and apply primarily to the dilator's resilient member or members. The terms stretch, tension, tensing, tensioning, elastic or elasticity are intended herein to apply to the elastic membrane. Strictly speaking, the terms resilient or resiliency may be applied to an object that exhibits either 'flexure' or 'elasticity'. However, for purposes of the present invention 'resilient' applies herein exclusively to a resilient member or members. Specifically, a resilient member is resilient; it flexes out-of-plane. An elastic membrane is elastic; it stretches in-plane. Both return at least substantially to their initial position after flexure or stretch, respectively. Dilators are usually manufactured in the unflexed, unstretched, initial position, and are flexed and/or stretched during application. Thus, embodiments may be described either as "capable of" flexing and/or stretching (when the embodiment is in an initial or rest position) or "flexed" and/or "stretched" (when the embodiment is in use).

The dilator directional element modifies, directs, affects or alters dilator spring biasing properties to enhance efficacy, engagement, useful duration, comfort, or ease of use. In the present invention, the elastic membrane directs the dilator's spring biasing properties, at least in part, to shift some delaminating peel and tensile forces generated by the resilient member(s) into shear forces extending somewhat parallel to the plane of the skin surface of the nose, both in a direction parallel to the dilator's length, and also perpendicular thereto, thus somewhat parallel to the bridge of the nose. The elastic membrane allows the resilient member(s) terminal ends to lift away from the surface of the nose, which creates less engagement contact surface area, and which may contribute to greater dilator comfort when in use. The elastic membrane and resilient member(s), combined, are the primary parts of the dilator's resilient element.

The directional element may further include one or more design features that, for example, spread spring biasing forces to a greater lateral extent of the dilator, increase or decrease localized spring biasing forces; mitigate or transform delaminating peel and tensile forces; direct spring biasing forces to discrete engagement contact points at each end region of the dilator; or create lessening of, or a gradient reduction of, spring biasing forces at one or both of the dilator's end regions.

The resilient element comprises at least one resilient member extending at least through the intermediate region of the dilator, and may include two or more resilient members adjacent and generally parallel each other, or that may overlay entirely one onto another, or overlap partially one onto another. A single resilient member may include components, such as resilient spring fingers extending outward from a common center, or the resilient member may be bifurcated laterally to form resilient spring fingers extending away from the dilator's intermediate region to one or both end regions of the dilator.

A plurality of resilient members may be vertically separated by a material layer interposed therebetween (such as the elastic membrane or a bonding layer) so as to separate resilient members into two or more resilient layers. The interposing material layer may comprise an adhesive substance or a flexible material, or both, and may further contribute to the engagement element of the dilator.

The peripheral dimensions of the dilator may be defined, in whole or part, by an element, a layer or portion thereof, or by any combination of layers. Dilator layers may be combined into a laminate, forming the dilator as a single body truss. The dilator/truss includes first and second end regions adapted to engage outer wall tissues of first and second nasal passages, respectively, and an intermediate region adapted to traverse a portion of a nose located between the first and second nasal passages.

It is an important objective of the present invention to incorporate an elastic membrane into the resilient element of novel nasal dilator devices. A further objective is to address the dynamic relationship between the engagement and resilient elements in nasal dilator devices used by athletes vs. home use. A still further objective is to provide greater comfort in nasal dilator devices by having a lesser engagement or contact surface area than that defined by the dilator's outer periphery. The present invention builds upon the prior art and discloses new, useful, and non-obvious external nasal dilators.

The present invention is not limited to the illustrated or described embodiments as these are intended to assist the reader in understanding the subject matter of the invention. The preferred embodiments are examples of forms of the invention comprehended by that which is taught, enabled, described, illustrated and claimed herein. All structures and methods that embody similar functionality are intended to be covered hereby. The nasal dilators depicted, taught, enabled and disclosed herein represent families of new, useful and non-obvious devices having a variety of alternative embodiments. Dilator elements, layers, members, components, materials, or regions may be of differing size, area, thickness, length, width or shape than that illustrated or described while still remaining within the purview and scope of the present invention.

Some embodiments of the present invention may refer to, or cross reference, other embodiments. It will be apparent to one of ordinary skill in the art that nasal dilator features, construction or configuration may be applied, interchanged or combined between and among the preferred embodiments.

For descriptive clarity, certain terms may be used in the specification and claims: Vertical refers to a direction parallel to thickness, such as the thickness of a finished article, a member or component, or a laminate. Horizontal refers to length or longitudinal extent, such as that of a finished article or element thereof, or a direction parallel thereto. Lateral refers to its width or lateral extent. Longitudinal also refers to length, perpendicular to width or lateral extent. A longitudinal centerline is consistent with the long axis of a finished device or element, bisecting its width midway between the long edges. A lateral centerline bisects the long edges of a finished device or element midway along its length, and is perpendicular to the longitudinal centerline. An object or objects referred to as adjacent or consecutive one another generally means laterally-parallel to, or consistent with, their width. Objects referred to as successive are generally oriented lengthwise, end to end. The terms upper and lower refer to object orientation, particularly in plan views, relative to the top and bottom of the drawing sheet.

Broken lines and dashed lines are used in the drawings to aid in describing relationships or circumstances with regard to objects:

A broken line including a dash followed by three short spaces with two short dashes therebetween indicates separation for illustrative purposes, such as in an exploded view, or to indicate an object or objects removed or separated from one or more other objects, primarily for illustrative clarity.

A dashed line (sometimes referred to as a shadow line) of successive short dashes with short spaces therebetween may be used to illustrate an object, such as one underneath another, or to reference environment such as facial features; or for clarity, to show location, such as the space an object or structure will occupy, would occupy, did occupy or may occupy; or for illustrative purposes, to represent an object, structure, element or layer(s) as transparent so that other objects more pertinent to the discussion at hand may be highlighted or more clearly seen.

A broken line including a long dash followed by a short space, a short dash and another short space is used to call out a centerline or an angle, or to indicate alignment; when accompanied by a bracket, to call out a section, segment or portion of an object or a group of objects; to illustrate a spatial relationship between one or more objects or groups of objects, or to create separation between objects for the purpose of illustrative clarity.

In the drawings accompanying this disclosure, like objects are generally referred to with common reference numerals or characters, except where variations of otherwise like objects must be distinguished from one another. Where there is a plurality of like objects in a single drawing figure corresponding to the same reference numeral or character, only a portion of said like objects may be identified. After initial description in the text, some reference characters may be placed in a subsequent drawing(s) in anticipation of a need to call repeated attention to the referenced object. Where a feature or element has been previously described, shadow lines, or dashed lines, may be used to generically illustrate the feature or element together with a generic reference character. Drawings are not rendered to scale, and where shown, the thickness of objects may be exaggerated for illustrative clarity.

BRIEF DESCRIPTION OF THE SEVERAL VIEWS OF THE DRAWING

FIG. 14 is a perspective view of the nasal dilator of FIG. 12.

FIG. 15 is an exploded perspective view of the nasal dilator of FIG. 13.

FIG. 16 is an exploded perspective view of an alternative form of the nasal dilator of FIG. 14.

FIG. 20 is a plan view of a nasal dilator in accordance with the present invention.

FIG. 21 is a perspective view showing the nasal dilator of FIG. 20 engaged to a human nose.

FIG. 22 is a cross-sectional view taken along the lines 2-2 in FIG. 20 showing the dilator secured to a skin surface of a user, the view aligned with a fragmentary plan view of the end region corresponding thereto.

DETAILED DESCRIPTION OF THE INVENTION

Figure 1:
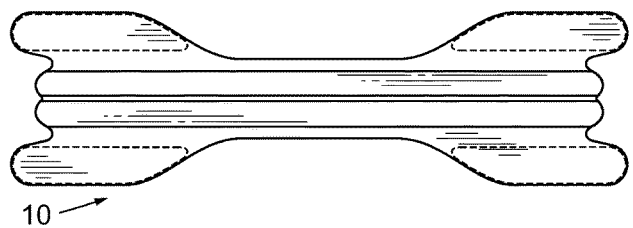
FIG. 1 is a plan view of a nasal dilator in accordance with the present invention.
Figure 2:
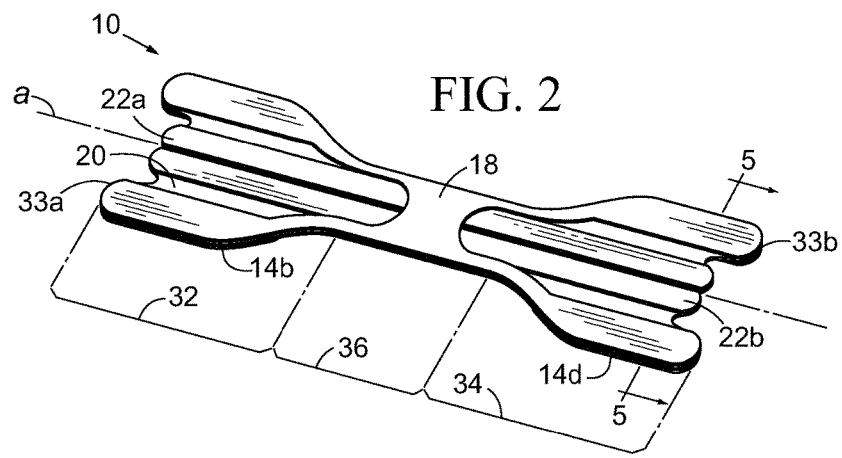
FIG. 2 is a perspective view of the nasal dilator of FIG. 1, further illustrating a cover layer member.

An embodiment of a form of a nasal dilator, 10, in accordance with the present invention, is illustrated in FIGS. 1-7. Dilator 10 comprises a laminate of several vertically stacked thin sheets, or layers, that correspond to the resilient and engagement elements. Dilator layers may include, for example, a contact layer, an elastic layer, and a resilient layer. The contact layer corresponds to the engagement element and provides the primary engagement element of the dilator. The elastic and resilient layers correspond to the resilient element. Dilator 10 may further include a cover layer, or a bonding layer. Dilator layers are preferably aligned along a longitudinal centerline, a, represented by a broken line as seen in FIG. 2.

Figure 3:
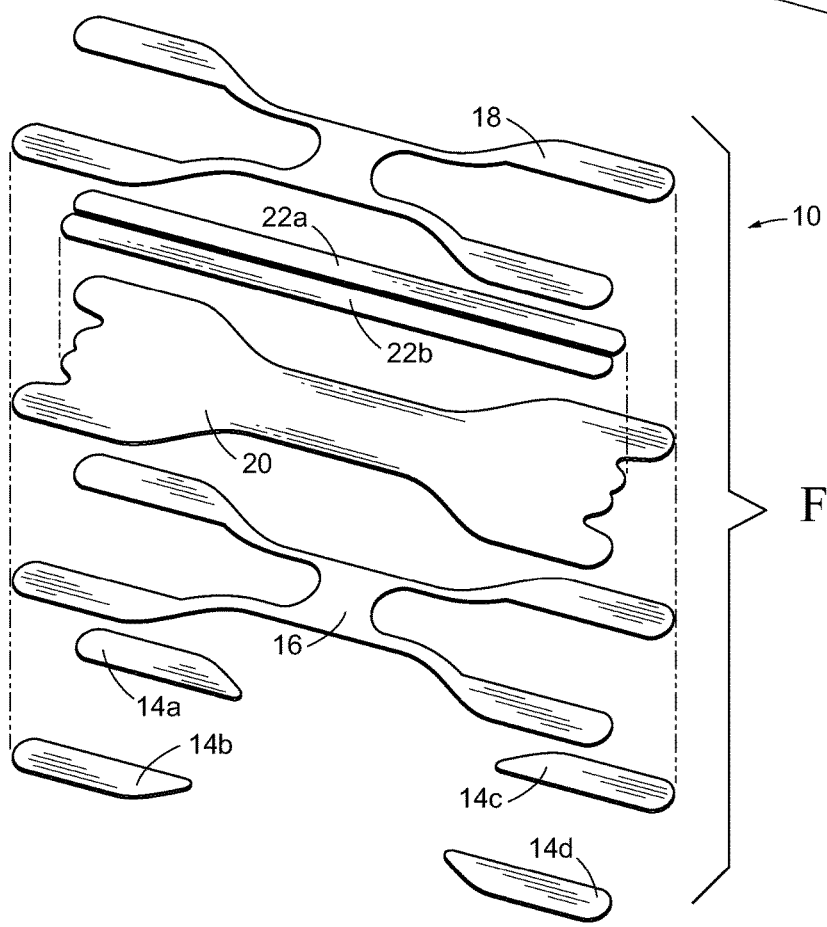
FIG. 3 is an exploded perspective view of the nasal dilator of FIG. 2.

A layer typically includes at least one member, and a member may further include one or more components. For example, the contact layer includes at least one contact member, 14, and may alternatively include a plurality of discrete engagement contact points from a plurality of contact members (e.g., 14*a*, 14*b*, 14*c*, etc.). A layer may include several members, or parts, or a single member may be bisected or divided into two or more parts. As seen in FIG. 3, for example, the contact layer includes four discrete, spaced apart members, 14*a*-14*d*, that provide four discrete engagement contact points for dilator 10 to engage the skin surface of the nose of a user.

The resilient element includes at least one resilient layer having at least one resilient member, 22 (if a plurality thereof. 22*a*, 22*b*, 22*c*, etc.). The elastic layer includes an elastic membrane, 20 (if a plurality thereof, 20*a*, 20*b*, 20*c*, etc.). An optional cover layer comprises at least one cover member, 18 (if a plurality thereof, 18*a*, 18*b*, 18*c*, etc.) For illustrative clarity FIG. 1 does not illustrate cover member 18, and contact members 14 are represented by dashed lines.

The elastic layer may be substantially coextensive with the periphery of dilator 10. It may define the dilator periphery, particularly in the absence of another layer doing so. Otherwise, the cover layer, bonding layer, or contact layer may define the dilator periphery, in whole or in part, or in combination with each other. Portions of any layer or member may overlap another layer or member.

A bonding layer member, 16 (if a plurality thereof, 16*a*, 16*b*, etc.), may be used to secure any two layers or members together. For example, FIG. 3 shows bonding member 16 interposed between contact members 14 and elastic membrane 20. Bonding member 16 may comprise an adhesive substance, such as, for example, a transfer or unsupported, adhesive. The bonding layer may also comprise a carrier material, or a carrier material with an adhesive substance disposed on one or both flat surface sides. Alternatively, the bonding member may comprise an adhesive disposed on a material layer such as that as may be used for the contact or cover members.

Dilator layers may be stacked, or vertically arranged, several different ways. Some layers, such as the contact, bonding, or cover layers, may be eliminated or interchanged. A portion of the elastic layer may contact the skin directly, in lieu of or in addition to a contact layer. The resilient layer may be positioned on top of or underneath the elastic layer. If the latter, both the contact member(s) and resilient member(s) would engage the same surface of the elastic membrane (as particularly depicted, for example, in FIGS. 20-23). A cover layer may be used to sandwich the elastic layer between it and the contact layer. And similarly, a contact member 14 may be formed as a base layer (as seen, for example, in FIG. 16) that may define the periphery of dilator 10.

Typically however, elastic membrane 20 is secured to contact member(s) 14 along the entire flat surface thereof opposite the skin-contact side. Similarly, elastic membrane 20 is most preferably secured to an entire flat surface side of resilient member(s) 22, particularly where the resilient member is positioned on top of the elastic membrane. If included in dilator construction, cover member 18 is most preferably configured so that it does not extend across the resilient layer at each end region of the dilator, as seen in FIG. 2, for example, so that the end portions of the resilient element may flex and stretch away from the surface plane of dilator 10.

Dilator layers or members may be secured to each other by any suitable means such as stitching or fastening, heat or pressure bonding or welding, ultrasonic welding, or the like, but are typically secured together by an adhesive substance disposed on at least a portion of one flat surface side of at least one member. In those instances where the resilient layer is on top—that is, uppermost—in the stacking order of dilator layers, it may be preferable to weld it to the layer to which it attaches or is primarily secured or affixed. A biocompatible adhesive for affixing or engaging dilator 10 to the skin of the nose is most preferably disposed on the skin engaging side of contact members 14 or other member or layer as may contact the skin.

The preferred materials for the contact and cover members may be selected from a range of widely available, preferably medical grade, flexible nonwoven synthetic fabrics or thermoplastic films that are preferably breathable and comfortable on the skin. Any suitable fabric or thermoplastic film, including various clear or colored films, including high Moisture Vapor Transmission Rate (MVTR) polyurethane film, may be used. A pressure sensitive adhesive, preferably biocompatible with external human tissue, may be disposed on at least one flat surface side of the material, in which case a protective, removable, release liner may cover the adhesive.

For use as the elastic membrane, a preferred material may be the same or similar to those for the contact and cover members, such as, for example, an ultra thin polyurethane film, a mesh, or a perforated material. The material preferably possesses in-plane elasticity, as discussed hereinbefore, particularly to a greater degree than, for example, that which may be present in materials chosen for the contact or cover members, and further having a range of elasticity that corresponds to the resiliency configured into the resilient member of dilator 10. A pressure sensitive adhesive may be disposed on the skin-engaging side of the material, or on any material layer or portion thereof that will contact the skin.

The preferred material for the resilient member is a thermoplastic resin, which may be selected from a material class having a range of flexural, tensile and elastic moduli so as to have substantial in-plane rigidity and out-of-plane flexibility, such that the resilient member has suitable spring biasing properties at a thickness, for example, of from about 0.005" to about 0.015".

The most preferred thermoplastic material from said class is a biaxially oriented polyester resin, Poly(ethylene terephthalate), (PET or boPET). PET is used in a number of medical device applications, is particularly suitable for nasal dilator devices, is widely available as an industrial commodity, and comes in a variety of standard, off-the-shelf forms. However, any plastic film having the same or similar tensile, flexural, or elastic modulus values would also be suitable. The preferred material may include a pressure sensitive adhesive disposed on one or both surfaces thereof.

Contact member 14 may alternatively include or comprise a thermoplastic film selected from the preferred materials for resilient member 22, which may be desirable, for example, where dilator 10 is configured to have a plurality of relatively small, discrete contact members 14. The material is preferably thinner, however, and thus more flexible, than that used for the resilient member. The in-plane rigidity of the material may allow elastic membrane 20 to pull more equally or uniformly on the entirety of the flat surface of contact member 14, and by extension, the skin surface engaged thereby. As a laminate, contact member 14 may comprise, for example, a spunlaced polyester fabric on the skin facing side together with a thin PET film on the opposite side.

A release liner may removably cover exposed adhesive from any layer preliminary to using the dilator. The shape and dimensions of the release liner may correspond to the periphery of dilator 10 or may exceed the periphery of one or more dilators 10. The release liner may be bisected into two parts, which may overlap or abut, so as to facilitate removal from the dilator prior to use, as is common in adhesively applied medical devices.

As further seen in FIG. 2, the layers of dilator 10 form a unitary, or single body, truss. (FIG. 2 includes all of the layers illustrated in FIG. 3.) The truss has contiguous regions indicated generally by broken lines and brackets, including a first end region, 32, a second end region, 34, and an intermediate region, 36, which joins first end region 32 to second end region 34. The width of intermediate region 36 may be narrower than the width of end regions 32 and 34. End regions 32 and 34 are adapted to engage outer wall tissues of the first and second nasal passages respectively. Each end region has a corresponding end edge, 33a and 33b extending between the respective long edges of dilator 10. Portions of any layer may define a region of the truss or a portion thereof, and the layers, members or components of dilator 10 may extend from one region to another.

Figure 4:
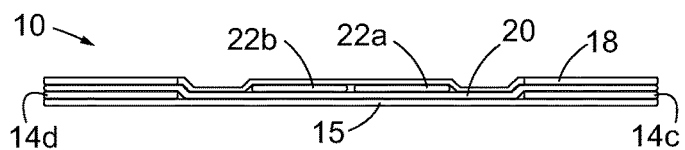
FIG. 4 is an end edge view of the dilator of FIG. 2, further illustrating a release liner backing.
Figure 5:
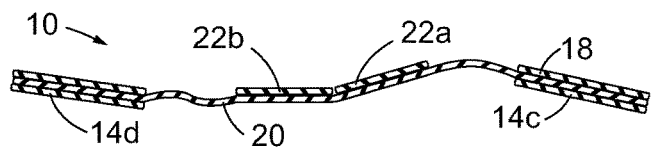
FIGS. 5 and 6 are cross sectional views, taken along the lines 5-5 in FIG. 2.
Figure 6:
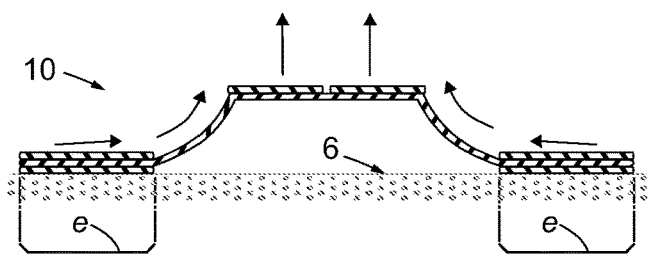

FIGS. 4-6 illustrate dilator 10 in a supported, an unsupported, and an elastic or tensioned state, respectively. FIG. 4, which is an end edge view, shows dilator 10 removably secured to a release liner, 15, which supports dilator 10 in a fixed, at-rest, position preliminary to use. The cross-sectional view of FIG. 5 illustrates that absent support from release liner 15, or being in contact with the nose of a user, contact members 14 may move freely relative to resilient members 22, the result of flexibility that may be inherent in the preferred material for elastic membrane 20.

Figure 7:
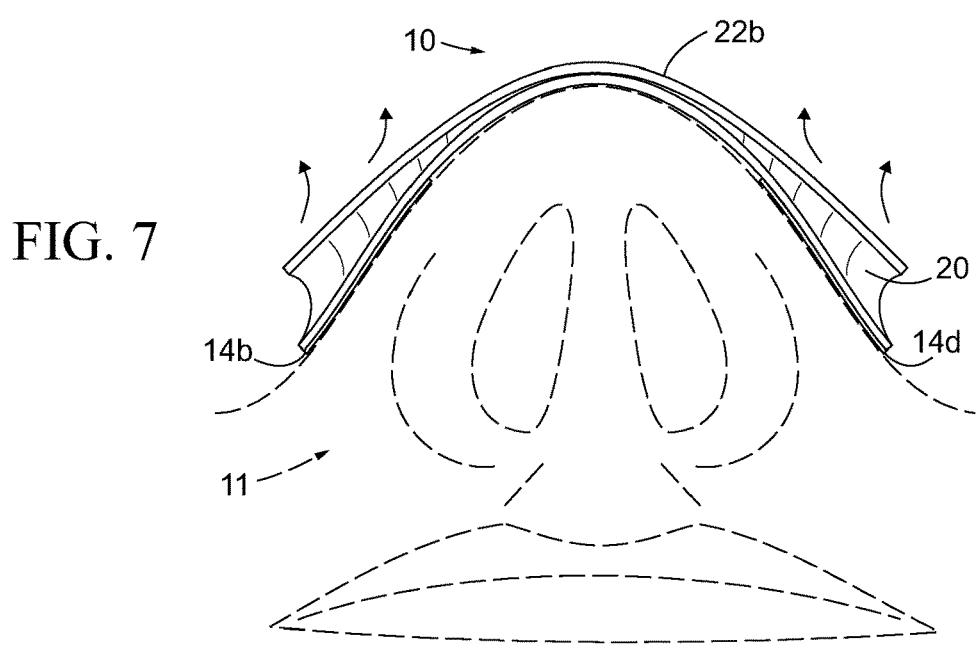
FIG. 7 is a perspective view of a portion of a face showing a front elevation, or long edge view, of the nasal dilator of FIG. 1 engaged to a human nose.

In use, however, as seen, for example, in FIGS. 6 and 7, dilator 10 is in a tensioned and spring biasing state by virtue of being engaged to the nose of a user. Contact members 14 are affixed to the skin surface, as seen in the cross-sectional view of FIG. 6, at discrete engagement contact points, e, indicated by broken lines and brackets. Contact points e correspond to the surface area(s) of contact member(s) 14.

As further seen in FIGS. 6 and 7, when in use, dilator spring biasing forces exert a pulling force on contact members 14 as indicated by directional arrows. The elasticity inherent in elastic membrane 20 allows vertical separation of the resilient member terminal ends from skin surface, 6, indicated by the two upwardly pointing arrows at the top center of FIG. 6. Directional arrows also indicate where said lifting creates at least some shear forces extending roughly parallel to skin surface 6.

Spring biasing forces extend from contact points e along that portion of the surface plane of elastic membrane 20 extending between contact members 14 and resilient members 22. FIG. 7 similarly illustrates portions of the resilient layer vertically separating from the skin surface, and the stretching of elastic membrane 20 when dilator 10 is engaged to a nose, 11. It should be noted that FIG. 7, and similar drawing figures herein that show elastic membrane 20 under tension, include short curved lines to indicate said stretching for purposes of illustrative clarity, regardless whether the preferred material would or would not, in practice, exhibit the same or similar stretch lines.

Figure 8:
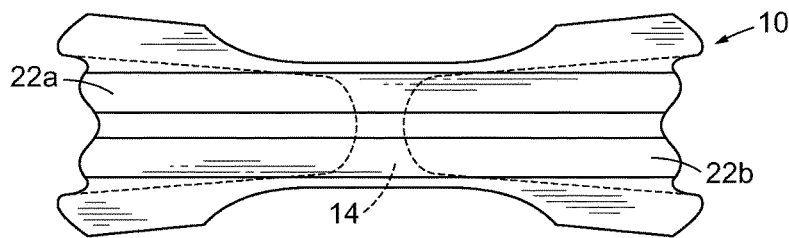
FIG. 8 is a plan view of a nasal dilator in accordance with the present invention.
Figure 9:
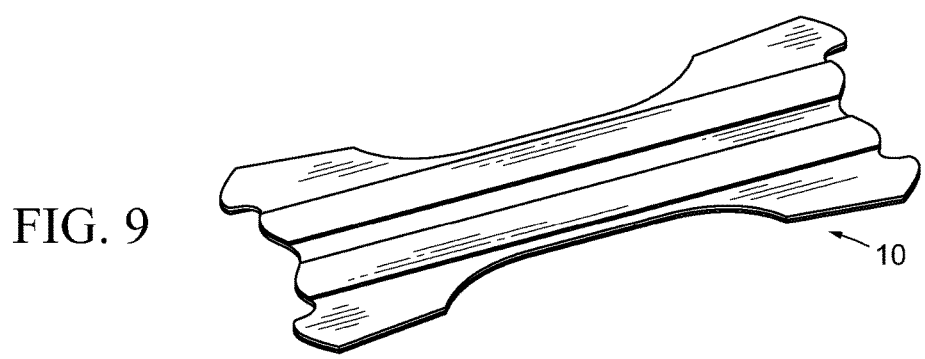
FIG. 9 is a perspective view of the nasal dilator of FIG. 8.
Figure 10:
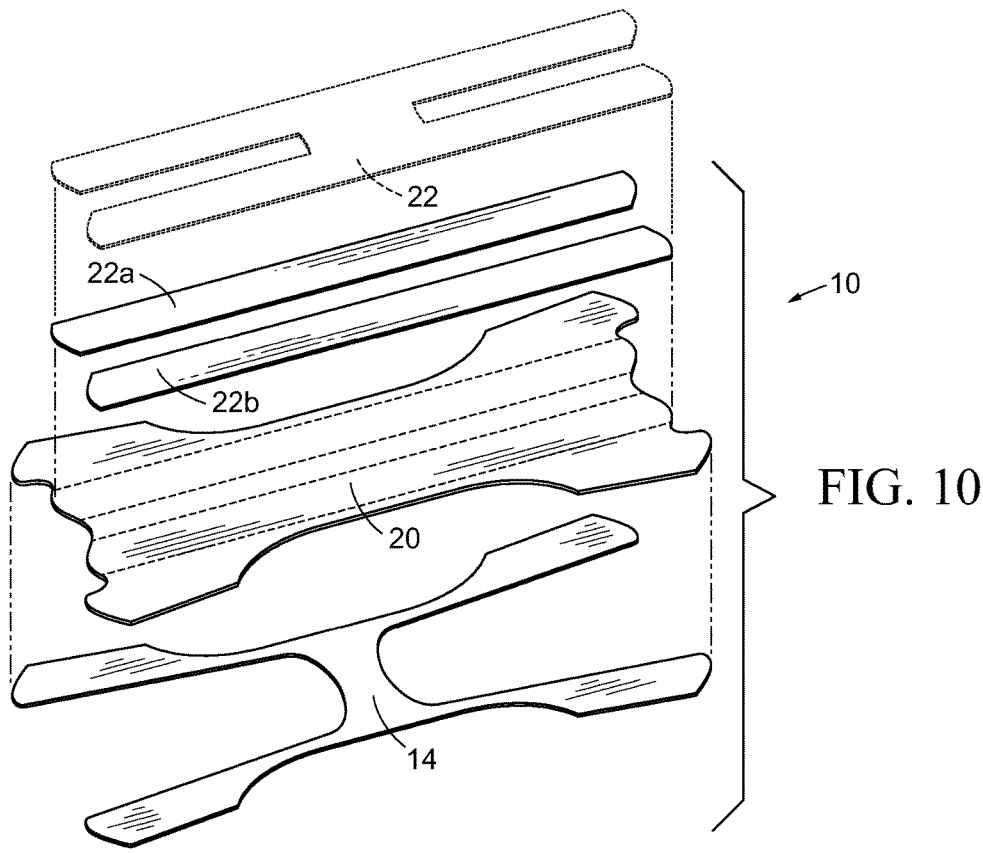
FIG. 10 is an exploded perspective view of the nasal dilator of FIG. 9.
Figure 11:
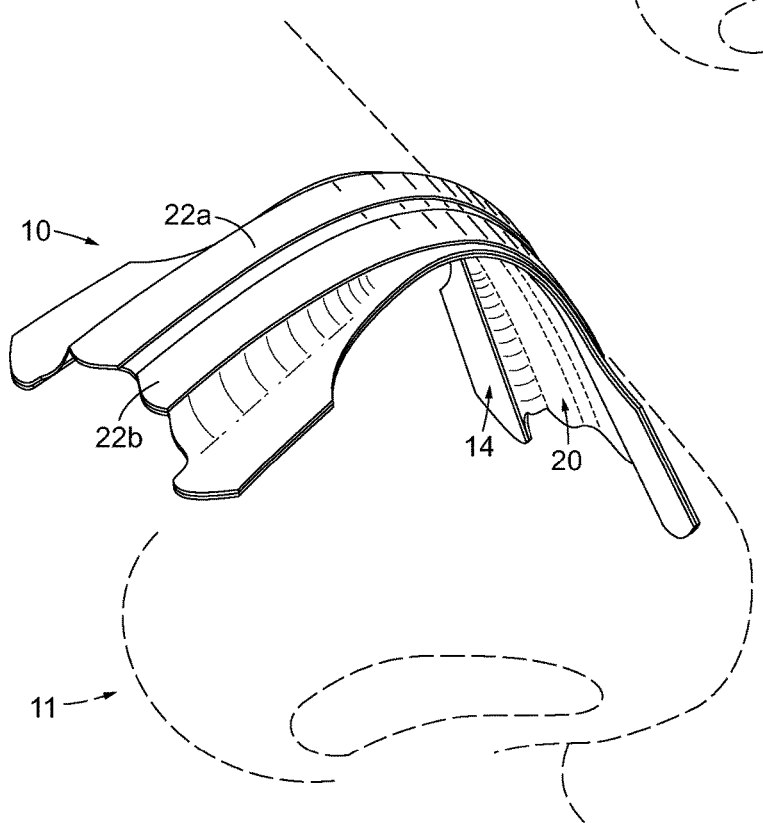
FIG. 11 is a three-quarter perspective view of a portion of a human nose showing the nasal dilator of FIG. 9 engaged thereon.

As seen in FIGS. 8 and 10, a single contact member 14 (represented by dashed lines in FIG. 8) is configured to extend along the peripheral long edges of dilator 10, and further to extend across the width of dilator 10 along at least a portion of intermediate region 36. FIG. 11 illustrates dilator 10 affixed to nose 11. (The nose is depicted in shadow lines as 'invisible', for illustrative clarity, such that a portion of the underside, or skin-engaging side, of dilator 10 may be seen.) The terminal ends of resilient members 22 separate from the skin at end regions 32 and 34. Elastic membrane 20 is shown tensioned, exhibiting in-plane elasticity, or stretch, between contact member 14 and the respective outer long edges of resilient members 22a and 22b.

Figure 12:
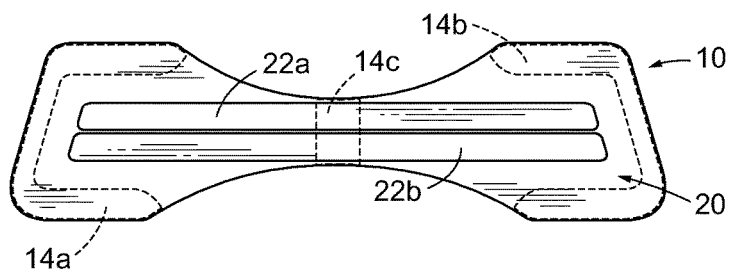
FIG. 12 is a plan view of a nasal dilator in accordance with the present invention.

FIGS. 8-11 illustrate resilient members 22a and 22b spaced further apart than, for example, the resilient members of dilator 10 shown in FIGS. 1 and 12. That portion of elastic membrane 20 extending between the respective inside long edges of the resilient members, by virtue of its in-plane stretch, allows greater relative movement between the resilient members than if they were closer together, or otherwise secured to a material having less in-plane elasticity.

FIG. 10 further illustrates that the resilient layer of dilator 10 may alternatively comprise a single resilient member 22, represented by dashed lines, configured to have a plurality of spring finger components extending outward from a common center. In the present embodiment the spring finger components are configured to emulate the effect of two parallel resilient members, but may otherwise be configured a variety of ways.

An embodiment of another form of dilator 10, in accordance with the present invention, is illustrated in FIGS. 12-15. The dilator end edges may be angled inward to correspond generally to the line where the nose meets the cheek of the user. Contact members 14a and 14b extend around the periphery of each end region 32 and 34, respectively. The resilient members' terminal ends are set inboard from the dilator peripheral end edges such that elastic membrane 20 extends around and outboard thereof.

Figure 13:
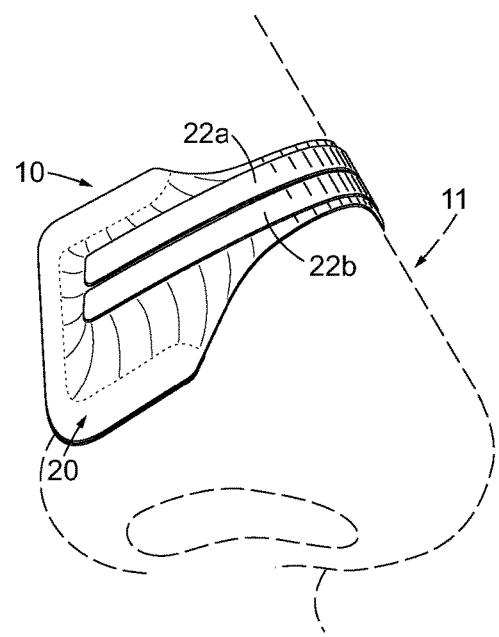
FIG. 13 is a three-quarter perspective view of a portion of a human nose showing the nasal dilator of FIG. 12 engaged thereon.

This configuration allows elastic membrane 20 to pull from the entire periphery of each end region, as particularly illustrated in FIG. 13, in which dilator 10 is depicted in use on nose 11. Dashed lines indicate the margin between where elastic membrane 20a is secured to contact member 14, and that portion which separates from the surface of nose 11. Contact member 14c is positioned directly over the bridge of the nose, interposed between elastic membrane 20 and the skin surface thereat. Contact member 14c may be non-adhering to the skin thereat, which may contribute to greater comfort.

As discussed hereinbefore, dilator layers may be configured and stacked several ways. FIG. 16 illustrates an alternative arrangement of dilator layers, for example, to that seen in FIG. 15. A base layer comprises a single contact member 14 having substantially the same peripheral shape as elastic membrane 20, and thus substantially defining the periphery of dilator 10. A plurality of bonding members, 16a-16c, having substantially the same peripheral shape as contact members 14 as seen in FIG. 15, secure contact member 14 to elastic membrane 20. And a single resilient member 22 is used in lieu of the two parallel resilient members as seen in FIG. 14.

Returning briefly now to separation of the resilient member terminal ends from the skin surface of the nose, as particularly seen in FIGS. 6-7, 11 and 13 (and in other embodiments to follow): Said separation allows a change in the angle of focused spring biasing forces thereat, at least in part, shifting, or transforming, at least some of those forces from primarily peel and tensile forces into primarily shear forces.

Transformed forces are imparted to contact member(s) 14, and by extension, to the end regions 32 and 34 of dilator 10. This is in contrast to a greater delaminating tendency resulting from primarily peel forces. Shear forces are typically more easily withstood by the adhesives typically used to engage dilator 10 to the skin surface than are peel forces. Accordingly, a smaller amount of adhesive (or a less-aggressive adhesive) may suffice to secure dilator 10 to the nose, which may contribute to user comfort as well as lower the manufacturing cost of dilator 10.

Figure 17:
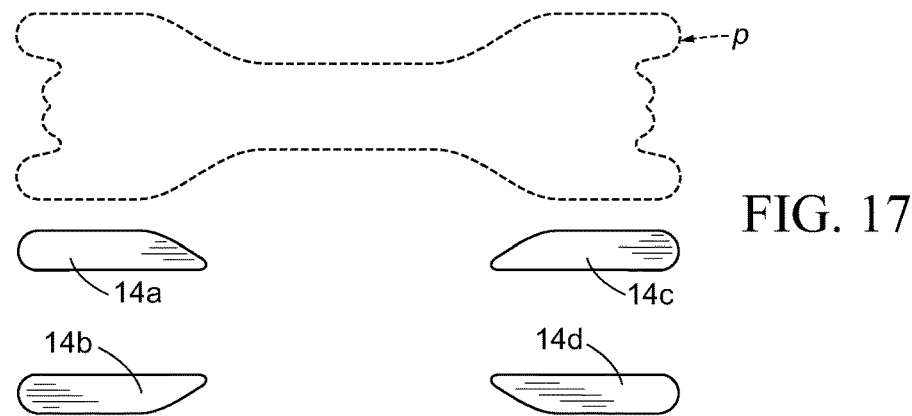
FIG. 17 is a plan view of the contact and peripheral defining layers or members, respectively, of the nasal dilator of FIG. 1.
Figure 18:
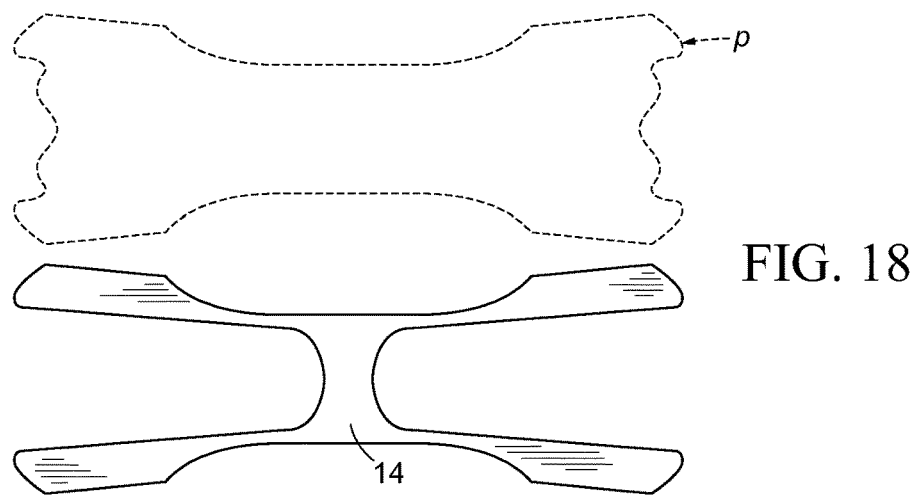
FIG. 18 is a plan view of the contact and peripheral defining layers or members, respectively, of the nasal dilator of FIG. 8.
Figure 19:
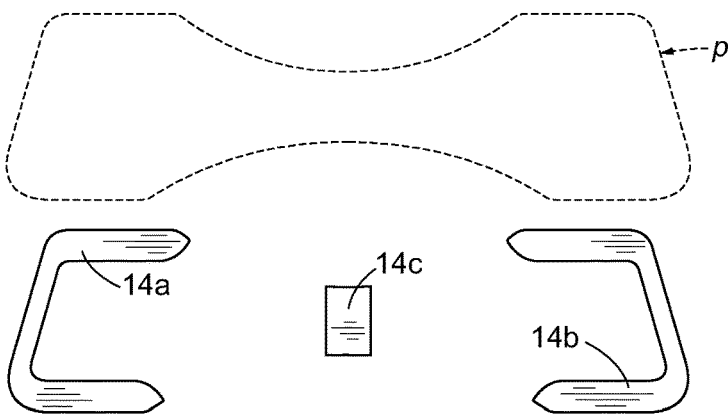
FIG. 19 is a plan view of the contact and peripheral defining layers or members, respectively, of the nasal dilator of FIG. 12.

Resilient member terminal ends separating from the skin surface of the nose means less dilator surface area contacting the skin, particularly less surface area that is adhesively engaged to the skin. Less skin-contacting surface area may contribute to greater user comfort. FIGS. 17-19 compares surface area between the overall periphery, p, of dilator 10 and the surface area of contact member(s) 14 actually touching the skin. FIGS. 17-19 correspond to the dilators of FIGS. 1, 8 and 12, respectively. Periphery p is depicted in broken lines, since the periphery of dilator 10 may be defined by a single layer or member, or a combination of dilator layers and/or members.

Using overall dimensions of roughly 2.75" length, and from 0.75" to 0.95" width, as may be typically found in the art, the total surface area of dilators 10, as defined by periphery p, as seen in FIGS. 17-19, is roughly 1.4, 1.8 and 1.3 square inches, respectively. The surface area of contact member(s) 14 shown in FIGS. 17-19 is roughly 0.46, 0.76 and 0.42 square inches, respectively, which is equal to about 32%, 43% and 32%, respectively, of the total surface areas of dilator 10. Accordingly, contact member surface area could reasonably fall within a range of from about 25% to about 70% of the total surface area of dilator 10.

Some embodiments of the present invention illustrate that resilient member(s) 22 may be affixed to the outer, or uppermost, side of elastic membrane 20. However, one or more resilient members may be alternatively positioned underneath elastic membrane 20, as seen, for example, in FIGS. 20-23. Additionally (but not specifically shown in the drawing figures), elastic membrane 20 or bonding member 16 may be used to vertically separate or divide a plurality of resilient members into two resilient layers; for example, one or more affixed underneath and one or more affixed on top thereof.

Where positioned underneath elastic membrane 20, resilient member(s) 22 may require little or no fixed engagement thereto. When under tension, as when secured to the nose, the resilient members would remain substantially held in place by the resilient membrane on top thereof. In such instances, the resilient member terminal ends may be removably secured to elastic membrane 20. That is, secured in such a way as to be removed without compromising the structural integrity of the dilator. Such an arrangement may allow resilient members, of various dimensions or configuration, for example, to be interchanged by the user. Accordingly, partially assembled nasal dilators, absent resilient members, for example, may be provided in kit form for final assembly and custom configuration by the end user.

Similarly, various forms of the constituent members of dilator 10 of the present invention, including contact members, bonding members, elastic membranes, resilient and cover members, etc., may also be provided in kit form; the constituent parts adapted for assembly and configuration by the end user, including means for affixing the members to each other so as to assemble the constituent layers of dilator 10 at least substantially as described herein.

FIGS. 1, 8 and 12 particularly illustrate the resilient layer of dilator 10 having two substantially parallel resilient members 22*a* and 22*b*. It will be apparent to those skilled in the art that a single resilient member 22 may be used in lieu thereof, as seen, for example, in FIG. 16.

Alternatively, any number of adjacent, generally parallel resilient members may be used, up to the limitations of the properties of the preferred material (which can only be slit so narrow), or otherwise that may fit within a workable width of dilator 10. Accordingly, it is believed that from two to about six resilient members is preferable, as particularly seen, for example, in FIGS. 33-38.

Multiple resilient members typically increase the axial, torsional, flexibility of dilator 10, which can lead to greater conformity to the irregular features and skin surface of the nose, and thus contribute to greater comfort of the dilator thereon. Torsional flexibility is enhanced by elastic membrane 20, particularly where substantially parallel resilient members are spaced laterally apart, as discussed previously with regard to FIGS. 8 and 10. That is, portions of elastic membrane 20 extending between their respective long edges may further enhance the ability of the resilient members to flex or otherwise move independently relative to each other.

FIGS. 20-32 illustrate embodiments of dilator 10 in accordance with the present invention wherein the resilient layer includes multiple resilient members, at least one of which having a divergent portion extending from intermediate region 36 into at least one end region of dilator 10. The resilient members are spaced relatively close together, side by side along substantially rectangular mid-sections, which allows intermediate region 36 to be narrower in width. Less width thereat generally corresponds to less skin-contacting surface area, which in turn may contribute to correspondingly greater user comfort.

As seen in the respective embodiments of FIGS. 20-23 and 25-28, two parallel resilient members are positioned relatively close together side by side, each member having substantially rectangular mid-sections. In one embodiment, both resilient members have divergent end portions. In the other embodiment, one resilient member is substantially rectangular from end to end, and the adjacent resilient member has divergent end portions. In either case, at least one resilient member end portion diverges laterally outward, spreading spring biasing forces across the enlarged end regions of dilator 10 and thus across a greater width than if the resilient member(s) remained substantially rectangular from end to end.

Figure 23:
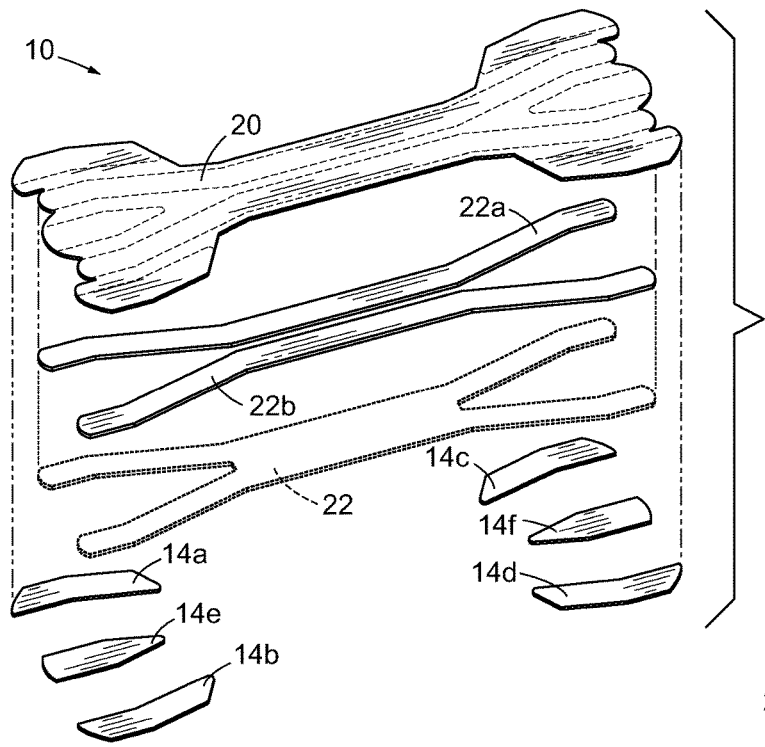
FIG. 23 is an exploded perspective view of the nasal dilator of FIG. 20.
Figure 27:
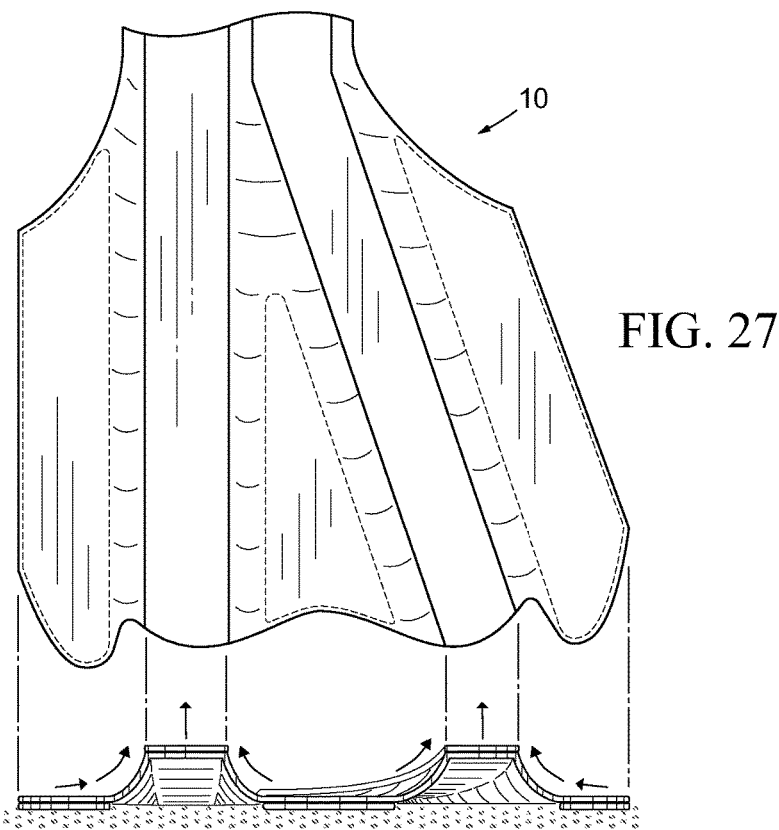
FIG. 27 is an end edge view of the dilator of FIG. 25 secured to a skin surface of a user, the view aligned with a fragmentary plan view of the end region corresponding thereto.
Figure 28:
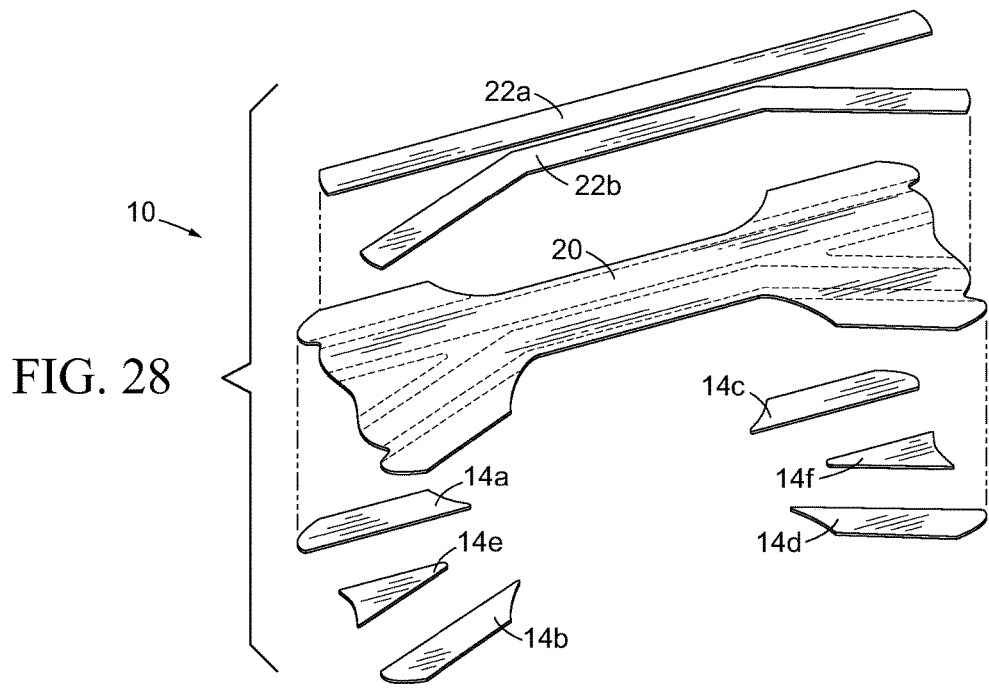
FIG. 28 is an exploded perspective view of the nasal dilator of FIG. 25.
Figure 29:
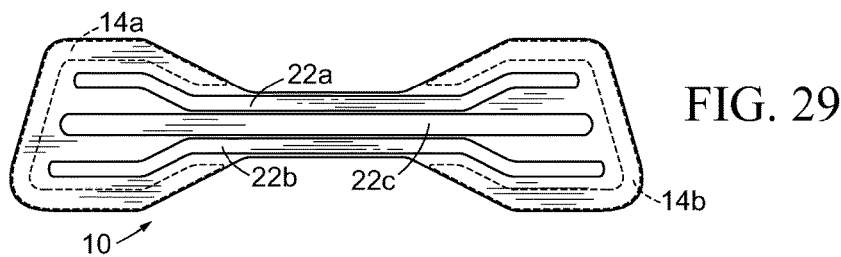
FIG. 29 is a plan view of a nasal dilator in accordance with the present invention.
Figure 30:
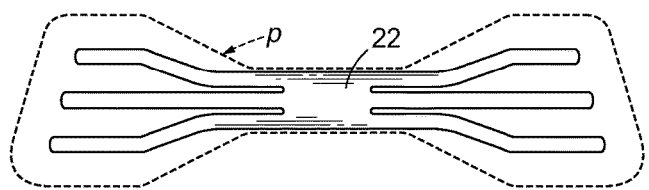
FIG. 30 is a plan view showing an alternative resilient element to the nasal dilator of FIG. 29.
Figure 31:
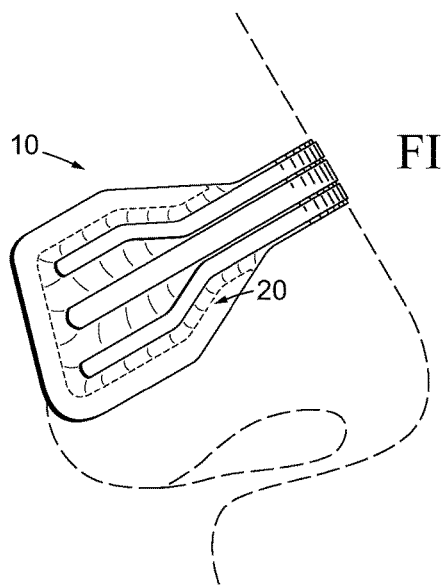
FIG. 31 is a perspective view showing the nasal dilator of FIG. 29 engaged to a human nose.

Enlarged end regions 32 and 34 each include three discrete engagement contact points, in the form of individual contact members 14*a*-14*f*, as particularly seen in FIGS. 23 and 28. (By comparison, FIG. 3, for example, illustrates two engagement contact points at each end region.) Contact members 14 are spaced apart across the width of each end region, positioned outboard the resilient members' long edges. FIGS. 22 and 27 include broken lines that indicate alignment of the resilient member terminal ends to the spaces between contact members 14.

The cross-sectional and end edge views, respectively, of FIGS. 22 and 27 further illustrate resilient member terminal ends pulling upward at the two discrete areas located between, and defined by, the three spaced apart contact members 14. Directional arrows indicate vertical separation of the resilient member terminal ends from skin surface 6 together with some shear forces extending roughly parallel thereto, as discussed hereinbefore.

Figure 24:
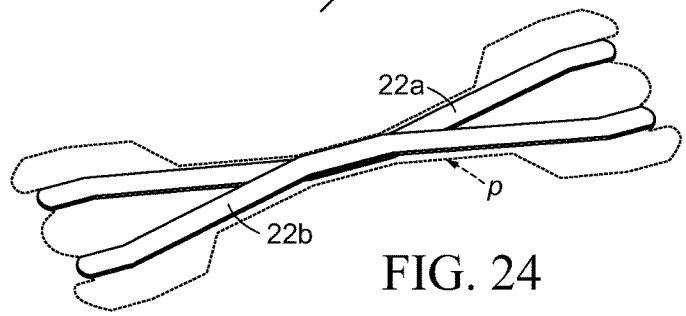
FIG. 24 is a perspective view illustrating an alternative resilient element to that of FIG. 23A.
Figure 25:
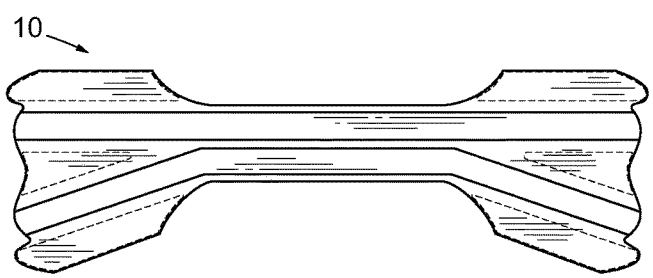
FIG. 25 is a plan view of a nasal dilator in accordance with the present invention.
Figure 26:
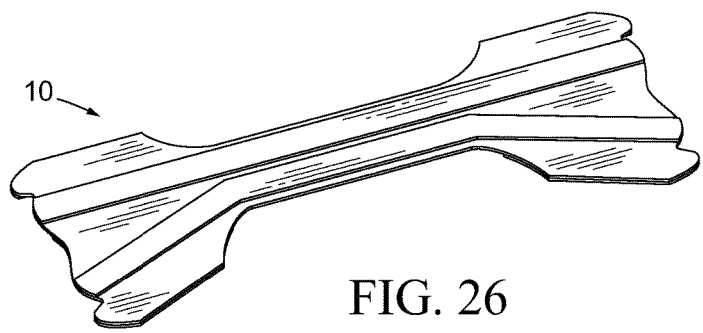
FIG. 26 is a perspective view of the nasal dilator of FIG. 25.

FIG. 23 illustrates by dashed lines that resilient members 22*a* and 22*b* may be formed as a single unit, resilient member 22, having divergent spring finger components extending outward from a common center. Alternatively, FIG. 24 illustrates that resilient members 22*a* and 22*b* may overlap, one onto another, which may allow the dilator periphery p to be narrower still at the intermediate region thereof. It will be apparent to the skilled artisan that the three resilient member configurations—side by side, overlapping or spring finger—may be generally similar in overall peripheral shape, and thus may be incorporated into similar peripheral configurations of dilator 10.

Resilient member terminal ends may be set inboard from the dilator end edges, as seen, for example, in FIGS. 12-16 and 29-37. Contact member 14 may thus extend around the peripheral edge of each dilator end region, as discussed hereinbefore. Divergent resilient member end portions position adjacent resilient member terminal ends laterally farther apart than would be the case with parallel rectangular resilient members.

Figure 32:
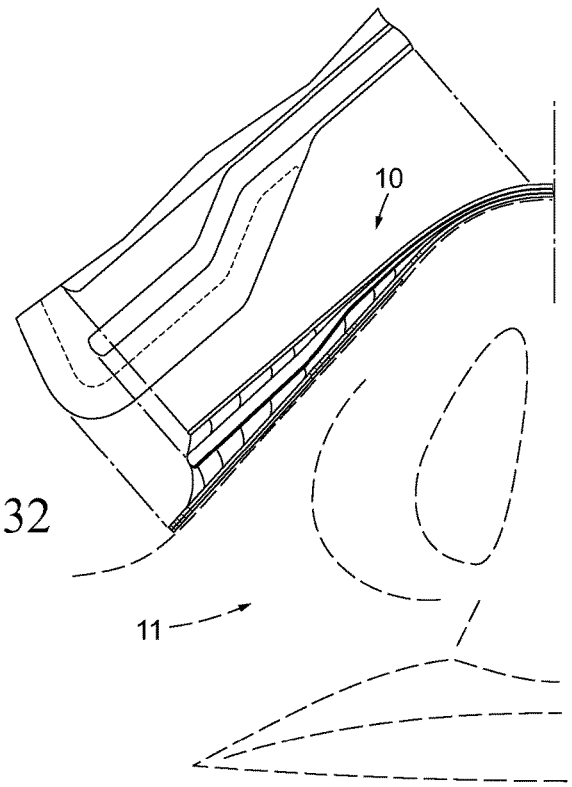
FIG. 32 is a fragmentary perspective view, taken on an enlarged scale, of a front elevation, or long edge view, of the nasal dilator of FIG. 29 engaged to the nose, the view aligned with a fragmentary plan view of the dilator end region corresponding thereto.

A middle resilient member may be configured to have a greater spring biasing force, for example, than the resilient members positioned adjacent to each side thereof. FIG. 32 particularly illustrates middle resilient member end portions and terminal ends thereof separating farther from the surface plane of the nose than the outer resilient members adjacent to each side. Broken lines extend between the long edge view and a fragmentary plan view to more particularly illustrate alignment of the resilient member terminal ends. An additional broken line indicates the centerline of nose 11.

Figure 35:
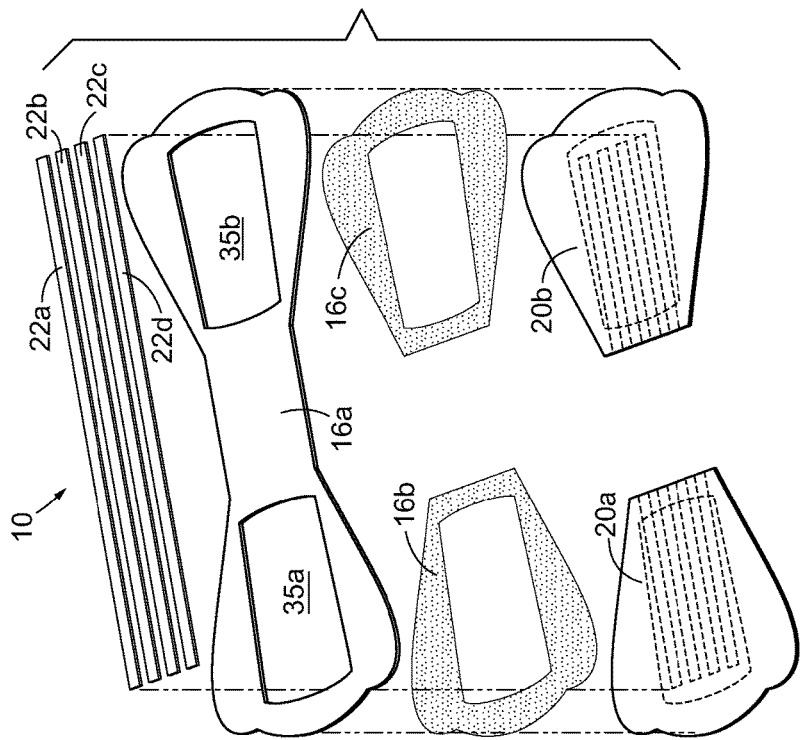
FIG. 35 is an exploded perspective view of the nasal dilator of FIG. 33.
Figure 33:
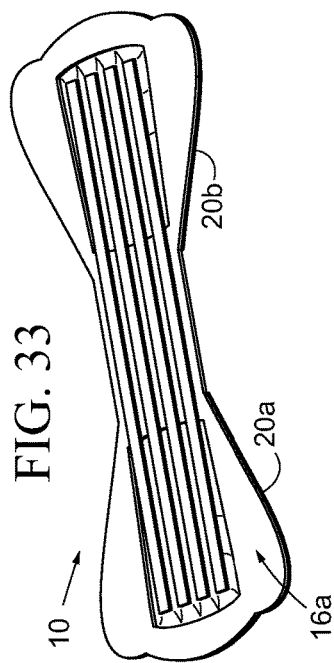
FIG. 33 is a perspective view of a nasal dilator in accordance with the present invention.
Figure 34:
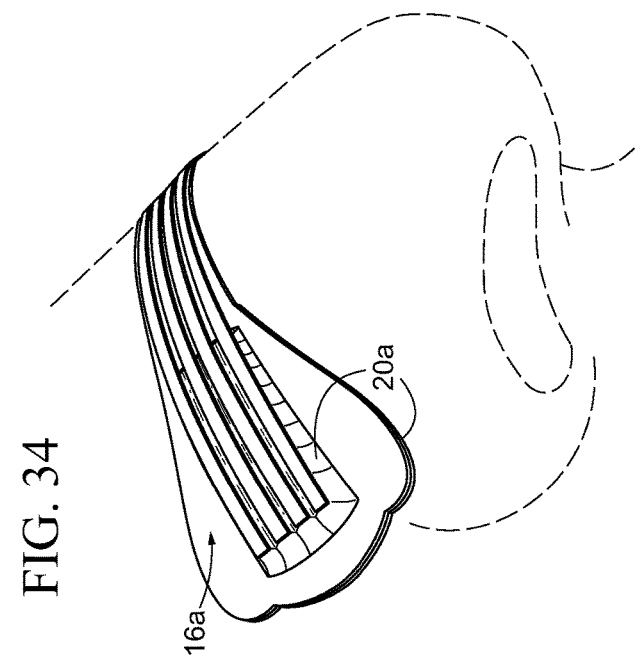
FIG. 34 is a three-quarter perspective view of a portion of a human nose showing the nasal dilator of FIG. 33 engaged thereon.

FIGS. 33-38 illustrate additional embodiments of dilator 10 in accordance with the present invention. As seen in FIGS. 33-35, terminal ends and end portions of a plurality of resilient members are secured to elastic membranes 20a and 20b through openings, 35a and 35b, at each end region, respectively, of dilator 10. FIG. 34 particularly shows resilient member end portions pulling upward and tensioning that portion of elastic membrane 20a extending through opening 35a. (Accordingly, reference character 20a in FIG. 34 points to two portions of the same elastic membrane: that which extends through opening 35, and that which is secured to the underside of bonding member 16a.) In this manner, a portion of elastic membrane 20 thus comes into contact with the skin surface.

FIG. 35 more particularly illustrates openings 35a and 35b formed in bonding member 16a. Elastic membranes 20a and 20b are secured to the underside (the skin-facing side) of bonding member 16a via bonding members 16b and 16c. Bonding members 16b and 16c define a surface area extending around the periphery of openings 35. Elastic membrane 20 is also secured to the end portions of resilient members 22a-22d positioned over openings 35 on the opposite, outer, side of bonding member 16a.

FIG. 35 particularly shows bonding member 16a as a single piece that substantially defines the periphery of dilator 10. (Bonding member 16a could alternatively be bisected into two parts, similar to the peripheral shape, for example, of elastic membranes 20a and 20b.) Similarly, elastic membranes 20a and 20b could be combined into a single unit. And as seen, for example, in FIG. 38, contact member 14 may be in the form of a base layer, as described hereinbefore.

Figure 38:
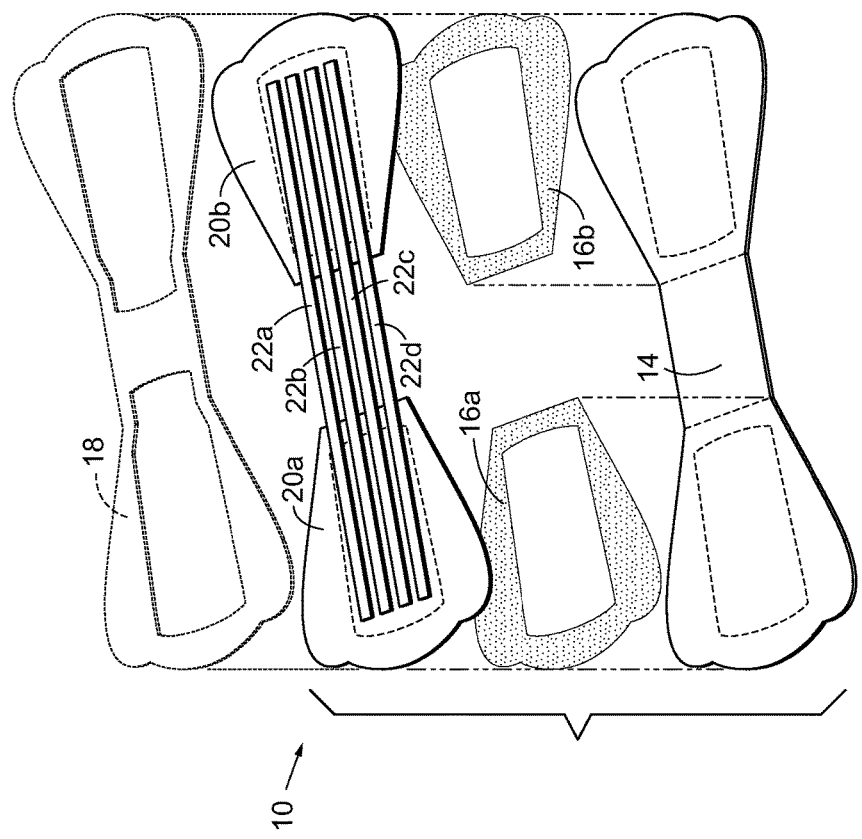
FIG. 38 is an exploded perspective view of the nasal dilator of FIG. 36.
Figure 36:
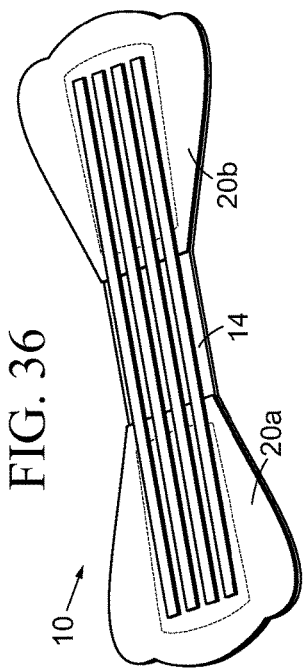
FIG. 36 is a perspective view of a nasal dilator in accordance with the present invention.
Figure 37:
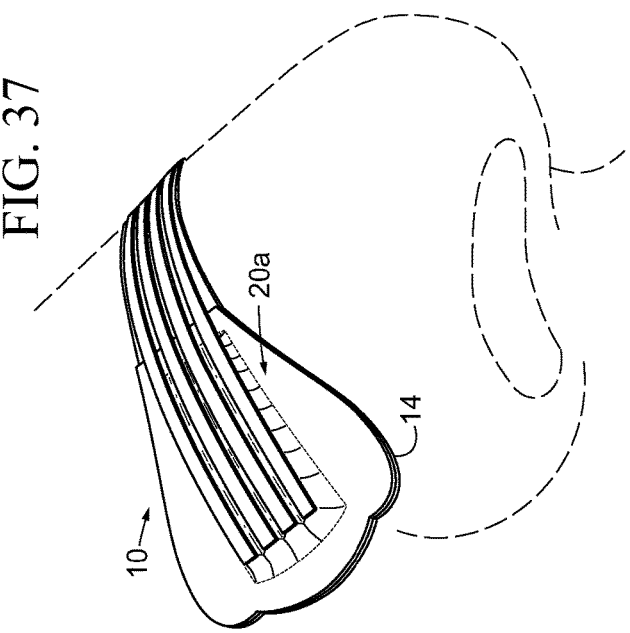
FIG. 37 is a three-quarter perspective view of a portion of a human nose showing the nasal dilator of FIG. 36 engaged thereon.

FIGS. 36-38 illustrate an alternative configuration to that of FIGS. 33-35 wherein elastic membranes 20a and 20b may be affixed to the outer, or top, side of contact member 14, secured thereto around a perimeter defined by bonding members 16a and 16b. Elastic membranes 20a and 20b (which may be combined into a single unit) are thus interposed between contact member 14 and resilient members 22, as particularly seen in FIG. 38. FIG. 38 further illustrates optional cover member 18, depicted in dashed lines, extending around the peripheral long edges of dilator 10 and across the width thereof at intermediate region 36, similar to the arrangement discussed previously with regard to FIGS. 2 and 3.

Openings (as shown in FIG. 35) are not required, since bonding members 16a and 16b secure elastic membranes 20a and 20b to portions of contact member 14 extending around a perimeter. Said perimeter leaves an unsecured area capable of separating from the surface of contact member 14. FIG. 37 particularly illustrates resilient member end portions pulling upward, tensioning the unsecured portion of elastic membrane 20a, to the extent the elasticity of elastic membrane 20 permits, as it separates from the surface plane of contact member 14. Dashed lines in FIG. 37 represent the margin between where elastic membrane 20a is secured to contact member 14, and the unsecured portion capable of separating therefrom.

The foregoing descriptions and illustrations are intended to reveal the scope and spirit of the present invention and should not be interpreted as limiting, but rather as illustrative of the inventive concepts and techniques thereof. Those skilled in the art to which the present invention is directed will appreciate that changes, modifications and alterations may be made—each such change, modification and alteration intended to be fully covered hereby—without departing from the scope of the invention.

We claim:

1. A nasal dilator, comprising:
an engagement layer for engaging the dilator to a skin surface of a nose of a user, the engagement layer comprising a thin material having an adhesive disposed thereon;
a resilient layer comprising at least one resilient member capable of providing resiliency in the form of spring biasing forces;
an elastic layer comprising an elastic membrane formed from a material web having flexural, tensile and elastic moduli so as to have in-plane elasticity and out-of-plane flexibility, the elastic membrane capable of providing stretching or tensioning forces in a direction parallel to a surface plane thereof, said engagement, resilient and elastic layers being separate and distinct from each other, and wherein
a portion of the elastic membrane interconnects the engagement layer and the at least one resilient member without contacting the skin surface when the nasal dilator is engaged thereto.

2. The nasal dilator of claim 1, wherein the at least one resilient member is formed from a thermoplastic resin having flexural, tensile and elastic moduli so as to have substantial in-plane rigidity and out-of-plane flexibility.

3. The nasal dilator of claim 1, wherein the stretching or tensioning forces extend between the engagement layer and the at least one resilient member when the dilator is in use, the stretching or tensioning forces extending primarily along a portion of opposite flat surfaces of the elastic membrane that are neither connected to the resilient member nor connected to the engagement layer.

4. The nasal dilator of claim 1, wherein the elastic layer is substantially coextensive with a periphery of the dilator.

5. The nasal dilator of claim 1, further comprising at least one bonding layer comprising at least one bonding member.

6. The nasal dilator of claim 1, wherein the engagement layer comprises at least one contact member in at least one contact layer for engaging the dilator to the skin surface.

7. The nasal dilator of claim 6 wherein the at least one contact member and the at least one resilient member are engaged to a same surface of the elastic membrane; or
a first surface of at least one contact member is configured to be engaged to the skin surface of a nose, and an opposite surface is engaged to the elastic membrane.

8. The nasal dilator of claim 6 wherein the at least one contact layer is selected from the group consisting of:

a) a plurality of contact members positioned at discrete engagement contact points in at least one end region of the dilator;
b) at least one contact member corresponds, at least in part, to a periphery of an end region of the dilator;
c) the at least one contact member defines a periphery of the dilator;
d) the at least one contact member is formed as a base layer; or
e) a contact member is formed as a base layer that is coextensive with a periphery of the dilator.

9. The nasal dilator of claim 1, wherein the resilient layer comprises at least one resilient member selected from the group consisting of:
a) at least one substantially oblong resilient band;
b) a plurality of substantially parallel resilient bands;
c) a plurality of spring fingers extending from a common center of at least one resilient member;
d) a resilient member having at least one divergent end portion extending away from another portion that extends substantially parallel to a long axis of the dilator; or
f) two resilient members that overlap at least partially onto one another.

10. The nasal dilator of claim 1 wherein the resilient layer comprises between two and six substantially parallel resilient bands spaced laterally apart; and
a portion of the elastic membrane extends between long edges of at least two adjacent resilient members so as to enhance torsional flexibility and ability of the resilient members to flex or otherwise move independently relative to each other.

11. The nasal dilator of claim 1 wherein at least one terminal end of the at least one resilient member is configured to separate from the skin surface when the dilator is engaged thereon, the separating and the stretching or tensioning forces transforming at least a portion of the spring biasing forces from peel forces to shear forces; and
the separating further adapted to create a reduced engagement contact surface area between an underside of the dilator and skin surfaces engaged by the engagement layer, the reduced contact surface area being within a range of from about 25% to about 70% of the surface area of dilator.

12. The nasal dilator of claim 1, configured so that when the dilator is engaged to the skin surface:
a) greater peel forces are exerted by the at least one resilient member than by the elastic membrane;
b) greater shear forces are exerted by the elastic membrane than by the at least one resilient member; and
c) at least a portion of the stretching or tensioning forces extend at least roughly parallel to the skin surface.

13. The nasal dilator of claim 1, further comprising a cover member.

14. A nasal dilator comprising:
a laminate including:
a resilient layer having in-plane rigidity and out-of-plane resilience,
an elastic layer having in-plane elasticity and out-of-plane flexibility, and
an engagement layer including an adhesive capable of adhering part but not all of a flat surface of the nasal dilator across a bridge of a nose of a user, wherein
a portion of the flat surface pulls away from skin of the nose when the dilator is engaged to and flexed across the bridge of the nose of the user, and wherein
a portion of the elastic layer is capable of being stretched between a portion of the resilient layer and an adjacent portion of the nasal dilator that is adhered to the skin of the nose, said portion of the elastic layer not adhered to or in contact with the skin of the nose.

15. The nasal dilator of claim 14, wherein the adhesive covers between about 25% and about 70% of a total plan-view area of the dilator.

16. The nasal dilator of claim 14 wherein the elastic layer is perforated.

17. A nasal dilator comprising:
a resilient member configured to flex across a bridge of a user's nose;
an engagement element configured to adhere to skin of the user's nose; and
an elastic membrane connecting the resilient member to a laterally-displaced portion of the engagement element so that a laterally-adjacent portion of the resilient member and the laterally-displaced portion of the engagement element are not in direct contact with each other, wherein
a portion of the elastic membrane is capable of being tensioned between the laterally-displaced portion of the engagement element and the laterally-adjacent portion of the resilient member when the engagement element is adhered to the skin of the user's nose and the resilient member is flexed across the bridge of the user's nose; and
the portion of the elastic membrane between the laterally-displaced portion of the engagement element and the laterally-adjacent portion of the resilient member does not contact the skin of the user's nose.

* * * * *